US012661447B2

(12) United States Patent
Mainz et al.

(10) Patent No.: US 12,661,447 B2
(45) Date of Patent: Jun. 23, 2026

(54) CHANNEL SYSTEM IN MEDICAL DEVICE TO HOUSE MATERIALS TO IMPROVE PERFORMANCE AND LONGEVITY

(71) Applicant: Becton, Dickinson and Company, Franklin Lakes, NJ (US)

(72) Inventors: Emilie Mainz, Morristown, NJ (US); Alex Chaves, Tyngsboro, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 704 days.

(21) Appl. No.: 17/921,763

(22) PCT Filed: Apr. 29, 2021

(86) PCT No.: PCT/US2021/029919
§ 371 (c)(1),
(2) Date: Oct. 27, 2022

(87) PCT Pub. No.: WO2021/222586
PCT Pub. Date: Nov. 4, 2021

(65) Prior Publication Data
US 2023/0158228 A1 May 25, 2023

Related U.S. Application Data

(60) Provisional application No. 63/018,401, filed on Apr. 30, 2020.

(51) Int. Cl.
*A61M 5/142* (2006.01)
*A61M 5/158* (2006.01)

(52) U.S. Cl.
CPC ........ *A61M 5/14248* (2013.01); *A61M 5/158* (2013.01); *A61M 2207/10* (2013.01)

(58) Field of Classification Search
CPC .............. A61M 5/14248; A61M 5/158; A61M 2207/10; A61M 5/165;
(Continued)

(56) References Cited

U.S. PATENT DOCUMENTS

| | | | |
|---|---|---|---|
| 4,537,680 A * | 8/1985 | Barth ..................... | B01D 29/44 210/498 |
| 5,108,377 A | 4/1992 | Cone et al. | |

(Continued)

FOREIGN PATENT DOCUMENTS

| | | |
|---|---|---|
| JP | 2019509873 A | 4/2019 |
| JP | 2020-032192 A | 3/2020 |

(Continued)

*Primary Examiner* — Theodore J Stigell
(74) *Attorney, Agent, or Firm* — Dickinson Wright PLLC

(57) ABSTRACT

A medical device operable to deliver a fluid to a patient, including a base having a base body and a hollow cannula for insertion into a patient, the hollow cannula being one of fixed to the base and movable relative to the base to a patient insertion position. The base body includes a fluid pathway that is one of fluidly connected with the hollow cannula and fluidly connectable with the hollow cannula. The fluid pathway includes a pathway portion sealed with a sealer, and the pathway portion includes an adsorbent operable to modify a fluid traversing the pathway portion by removing one or more compounds or substances from the fluid prior to delivery of the fluid to the patient through the hollow cannula.

20 Claims, 13 Drawing Sheets

(58) Field of Classification Search
CPC ........... A61M 2005/14252; A61M 2005/1586;
A61M 2005/1652; A61M 2205/759;
A61M 5/162
See application file for complete search history.

(56) References Cited

U.S. PATENT DOCUMENTS

| | | | |
|---|---|---|---|
| 7,976,532 B2 | 7/2011 | Kitani et al. | |
| 9,056,163 B2 | 6/2015 | Wu et al. | |
| 2007/0219501 A1* | 9/2007 | Kriesel ............... | A61M 5/1454 |
| | | | 604/185 |
| 2016/0354542 A1 | 12/2016 | Ward et al. | |
| 2019/0054233 A1 | 2/2019 | Demaria et al. | |
| 2020/0001006 A1 | 1/2020 | Pizzochero et al. | |
| 2020/0155755 A1* | 5/2020 | Chaves ............. | A61M 5/14248 |

FOREIGN PATENT DOCUMENTS

| | | | |
|---|---|---|---|
| WO | WO-2017180708 A1 | | 10/2017 |
| WO | WO-2019/209644 A1 | * | 10/2019 |

* cited by examiner

102

400

PROVIDING AT LEAST ONE OF A PATCH
INJECTOR, A BASE, A FLUID CONNECTOR, AND
A PUMP CONNECTOR   THAT INCLUDES A
GROOVE RECESSED FROM A
SURFACE THERE OF          —402

PROVIDING ADSORBENT IN GROOVE          —404

SEALING GROOVE WITH FILM TO FORM AT          —406
LEAST A PORTION OF A FLUID PATH

CHANNEL SYSTEM IN MEDICAL DEVICE TO HOUSE MATERIALS TO IMPROVE PERFORMANCE AND LONGEVITY

CROSS-REFERENCE TO RELATED APPLICATION

This application claims the benefit of U.S. provisional Application No. 63/018,401, filed Apr. 30, 2020, in the U.S. Patent and Trademark Office, the disclosures of which are incorporated herein by reference in its entirety.

FIELD OF THE INVENTION

The present invention relates generally to a medical device for delivering a fluid to a patient and filtering or removing selected compounds from the fluid before delivery to the patient. The medical device includes an adsorbent material disposed within the device, to remove selected compounds from the fluid just prior delivery of the fluid into the patient. The medical device in one embodiment is suitable for delivering a controlled dosage of an insulin formulation where the device is associated with an adsorbent for removing stabilizing agents and/or selected compounds from the insulin formulation prior to delivery to the patient.

BACKGROUND OF THE INVENTION

Insulin and other injectable medications are commonly delivered with patch injectors and infusion sets.

Drugs and pharmaceuticals often contain preservatives and/or stabilizing agents to extend the shelf-life of the drug or pharmaceutical. For example, insulin often contains phenol and/or m-cresol as stabilizers. These stabilizers can often produce side effects, such as irritation, inflammation, scarring, and lipohypertrophy at the injection site.

Existing infusion sets are disclosed in PCT Application PCT/US2019/028248, filed Jun. 28, 2019, the entire contents of which is hereby incorporated by reference Although the prior devices have been suitable for the intended use, there is a continuing need in the industry for improved medical devices to reduce the irritation and inflammation at the injection site.

SUMMARY OF EMBODIMENTS

Accordingly, it is an aspect of the present invention to provide a medical device to reduce irritation and inflammation at an injection site.

The foregoing and/or other aspects of the present invention are achieved by providing a medical device operable to deliver a fluid to a patient. The medical device includes a base having a base body and a hollow cannula for insertion into a patient, the hollow cannula being one of fixed to the base body and movable relative to the base body to a patient insertion position. The base body includes a fluid pathway that is one of fluidly connected with the hollow cannula and fluidly connectable with the hollow cannula. The fluid pathway includes a pathway portion sealed with a sealer, and the pathway portion includes an adsorbent operable to modify a fluid traversing the pathway portion by removing one or more compounds or substances from the fluid prior to delivery of the fluid to the patient through the hollow cannula.

The foregoing and/or other aspects of the present invention are also achieved by providing a medical device including a base having a hollow cannula for insertion into a patient, and a base body attached to the hollow cannula. The device also includes a fluid connector connectable to the base. The device also includes a pump connector connectable to a pump. Each of the base body, the fluid connector, the pump connector, and the tubing has a fluid pathway therethrough. The respective fluid pathways being fluidly connectable. The fluid pathway of at least one of the base body, the fluid connector, and the pump connector includes a pathway portion sealed with a sealer; and the pathway portion includes an adsorbent configured to modify a fluid traversing the pathway portion by removing one or more compounds or substances from the fluid prior to delivery of the fluid to the patient.

The foregoing and/or other aspects of the present invention are also achieved by providing a method of manufacturing a medical device. The method includes providing at least one of a patch injector, a base, a fluid connector, and a pump connector that includes a groove recessed from a surface of the at least one of the patch injector, the base, the fluid connector, and the pump connector. The method also includes providing an adsorbent in the groove, and sealing the groove with a sealer to form at least a portion of a fluid path through the at least one of the patch injector, the base, the fluid connector, and the pump connector.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
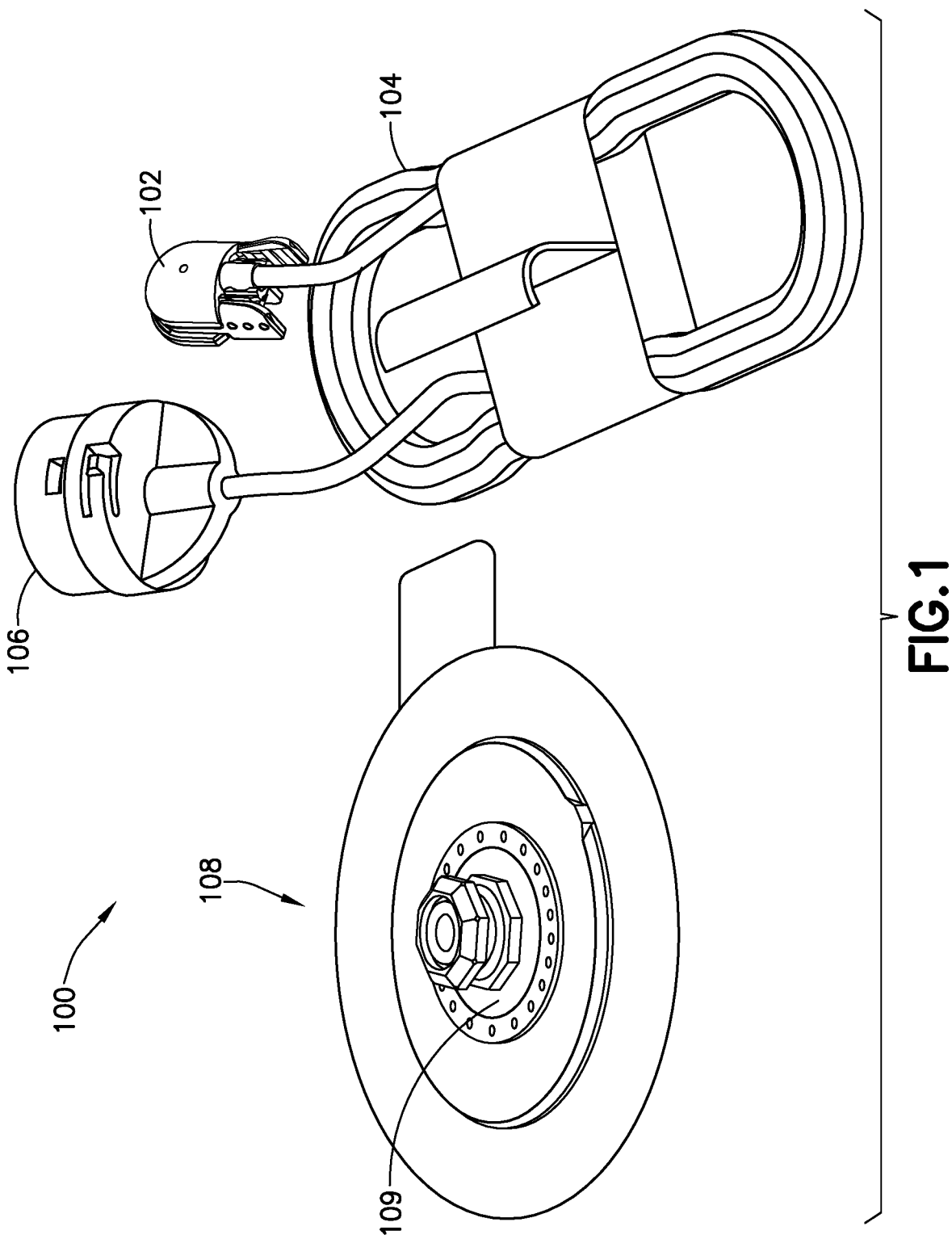
FIG. 1 illustrates an infusion set in accordance with an embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

The embodiments are not intended to be mutually exclusive so that the features of one embodiment can be combined with other embodiments as long as they do not contradict each other.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items.

Unless limited otherwise, the terms "connected," "coupled," and "mounted," and variations thereof herein are used broadly and encompass direct and indirect connections, couplings, and mountings. In addition, the terms "connected" and "coupled"" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

Embodiments of the present invention are directed to a medical device or medical delivery device and method of manufacturing a medical device that receives or carries a fluid, such as insulin, medication, or a drug for delivery to a patient, and removes one or more compounds or substances from the insulin, medication, or drug, and subsequently delivers the modified fluid to the patient.

The medical device is particularly suitable for use in delivering insulin that contains a stabilizer or preservative so that at least a portion of the stabilizer or preservative is removed from the insulin before delivering the modified insulin to the patient. The medical device for introducing an insulin formulation into the patient is used in association with an adsorbent material that contacts the insulin formulation before introduction to the patient.

The medical device can deliver the fluid, such as insulin, to a patient by a bolus flow delivery and/or basal delivery. In one embodiment, the drug is an insulin formulation or solution that is delivered to the patient in a selected and controlled dosage at an injection or infusion site.

The insulin formulation is typically a solution containing a preservative and stabilizing agent to extend the shelf-life of the insulin solution until ready for use. The stabilizing agent in one embodiment is phenol, m-cresol and mixtures thereof. The majority of Type I diabetics, and a subset of Type II diabetics, manage the condition by multiple daily injections of insulin. The daily injections result in side effects including irritation, inflammation, scarring, and lipo-hypertrophy and the accumulation of subcutaneous fat at the insulin injection site or infusion site. The presence of phenol and m-cresol in insulin formulation is effective as a bacteriostat and for stabilizing the insulin formulation. But the presence of the phenol and m-cresol in the insulin with repeating or sustained injection at an injection site or infusion site can cause inflammation and irritation to the patient and can reduce insulin absorption at the site and reduce longevity of the insulin delivery site.

The phenolic excipients m-cresol and phenol present in insulin analog formulations as a bacteriostatic and stabilizing factor are cytotoxic in an in vitro system and contribute to adverse tissue reactions when delivered locally at formulation concentrations. The adverse tissue reactions result in increased pro-inflammatory cytokine levels and altered subcutaneous insulin pharmacokinetics. The deleterious reactions are often dose-dependent, so that as more excipient is delivered, such as in insulin infusion devices, pharmacokinetics are increasingly altered relative to initial values. Test data suggests that excipient-induced models of inflammation negatively affect the route of insulin administration and absorption. This can lead to issues of inadequate adherence.

One feature of the inventive medical device is to remove the phenolic excipients selectively from insulin formulations without interfering with the effectiveness of the insulin upon delivery to the patient. Experiments using activated charcoal as an adsorbent show the effective removal of the phenol and m-cresol from insulin formulation while maintaining the effluent insulin at formulation concentrations. The resulting treated insulin having a reduced concentration of the phenolic excipient is delivered to the patient within a period of time where substantially no denaturing or loss of potency of the insulin occurs. In one embodiment, the adsorbent is selected to remove only the phenolic excipients.

The adsorbent can be used with the medical device for removing at least a portion of the stabilizing agents, and particularly for removing at least a portion of the phenolic stabilizing agents from an insulin formulation prior to introducing to the patient.

In one embodiment, the adsorbent is activated charcoal that can be in a granular, extruded, or powder form to provide a contact surface area for the insulin that is sufficient to remove a selected amount of the phenolic stabilizers to inhibit inflammation at the delivery site without denaturing or loss of potency of the insulin at the time of delivery to the patient. In the present description of the device and method, the terms activated charcoal and activated carbon are used interchangeably. Acid treated activated charcoal, such as phosphoric acid activated carbon, is particularly suitable for removing phenol and m-cresol from insulin formulations. In one embodiment, the activated charcoal is a chemically active carbon obtained by treatment with phosphoric acid. The activation can be by phosphoric acid, for example, at pH 6.7. One skilled in the art will understand, however, that other pH levels can be employed. Commercially available phosphoric acid treated activated charcoal can be used for the removal of phenol and m-cresol from insulin formulations. An example of a commercially available acid treated activated charcoal is available under the trade name CN5-20 by Cabot Corporation. The activated charcoal has a surface area to provide sufficient contact with the insulin to remove an amount of the phenolic compounds sufficient to minimize irritation and inflammation at the injection site.

The activated charcoal can be obtained from a variety of carbon sources including, for example, wood, coconut shell, olive pits, peat, lignite, coal or another suitable carbon source. The activation in one embodiment is by chemical activation with phosphoric acid to provide the beneficial porosity, pore volume, surface area, surface chemistry, and pore size distribution. The activated charcoal typically has a surface area of greater than 1,000 m²/g. The activated charcoal can have a pore volume of about 0.26-1.16 cm³/g, and generally about 0.40-0.70 cm³/g. In other embodiments, the activated charcoal can have a surface area of 1500 m²/g or greater. In further embodiments, the activated charcoal can have surface area of greater than 2300 m²/g and in some circumstances a surface area of greater than 3,000 m²/g depending on the method of activation.

The adsorbent is present in an amount to provide a contact time with the insulin formulation that is sufficient to remove a desired amount of the phenol, m-cresol or other stabilizing agents contained in the insulin formulation to reduce irritation and inflammation at the injection site without denaturing and without reducing the potency of the insulin. The adsorbent is located in the flow path of the insulin formulation as close to the injection member or delivery site as reasonably possible to limit degradation of the insulin formulation before introducing to the patient.

The amount of activated charcoal in the assembly complements the dosage and flow rate of the insulin depending on the delivery by basal flow or bolus flow delivery to provide the desired rate of adsorption of the phenolic stabilizers. In one embodiment, the amount of the adsorbent provides removal of about 95% of the m-cresol after 4 days and about 60% after 7 days at a basal flow rate.

Figure 6:
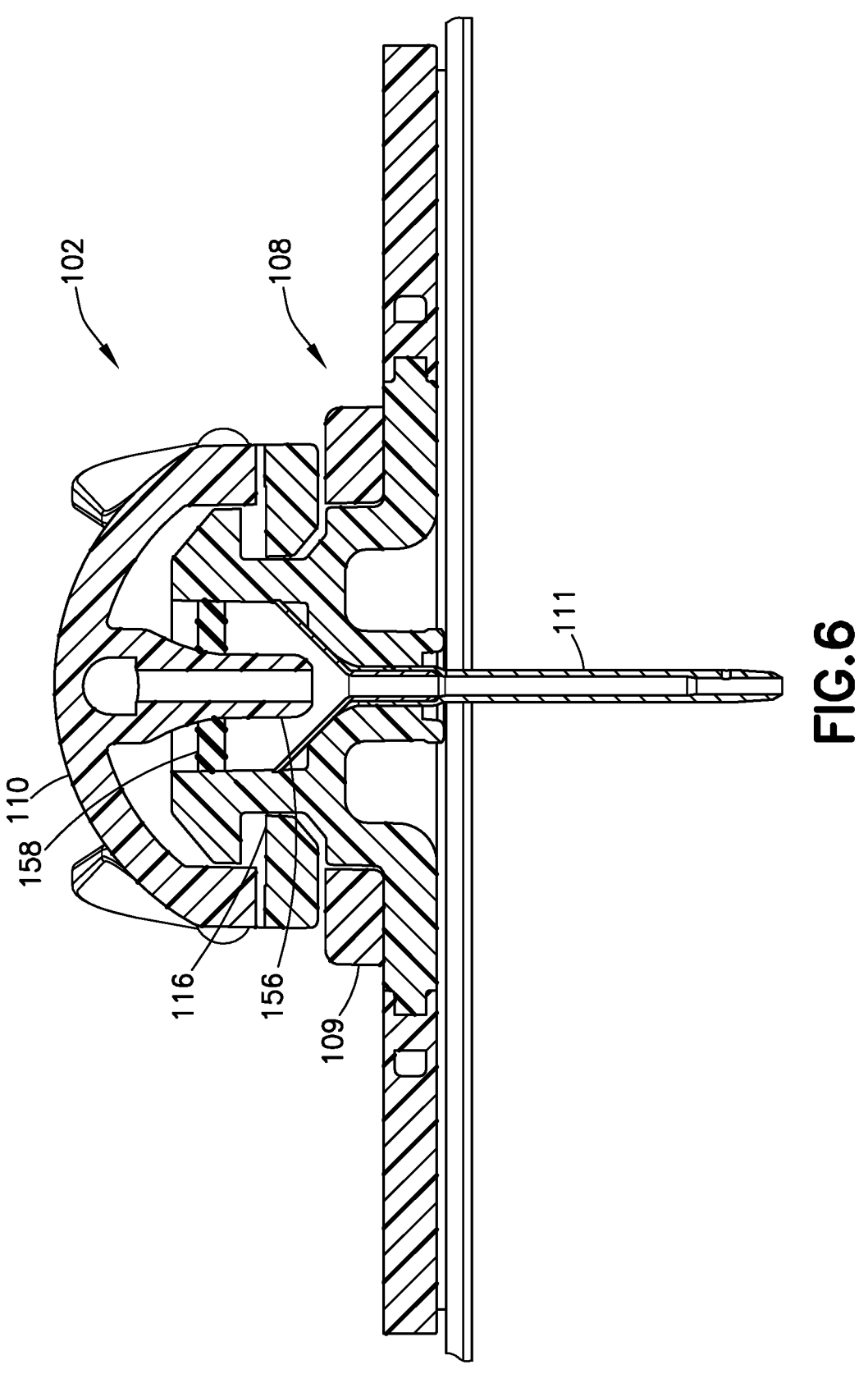
FIG. 6 is a cross sectional view of the fluid connector of FIG. 2 connected with a base of FIG. 2

FIG. 1 illustrates an infusion set 100 in accordance with an embodiment of the present invention. As shown, the infusion set 100 includes a fluid connector 102 connected with tubing 104 that is also connected to a pump connector 106 for connecting to a pump. The infusion set 100 also includes a base 108, which includes a base body 109 and a hollow cannula 111 (best seen in FIG. 7) for insertion into a patient. The fluid connector 102 is connectable to a top of the base 108, as shown in FIG. 6. Each of the base body 109, the fluid connector 102, the pump connector 106, and the tubing 104 has a fluid pathway therethrough.

Figure 2:
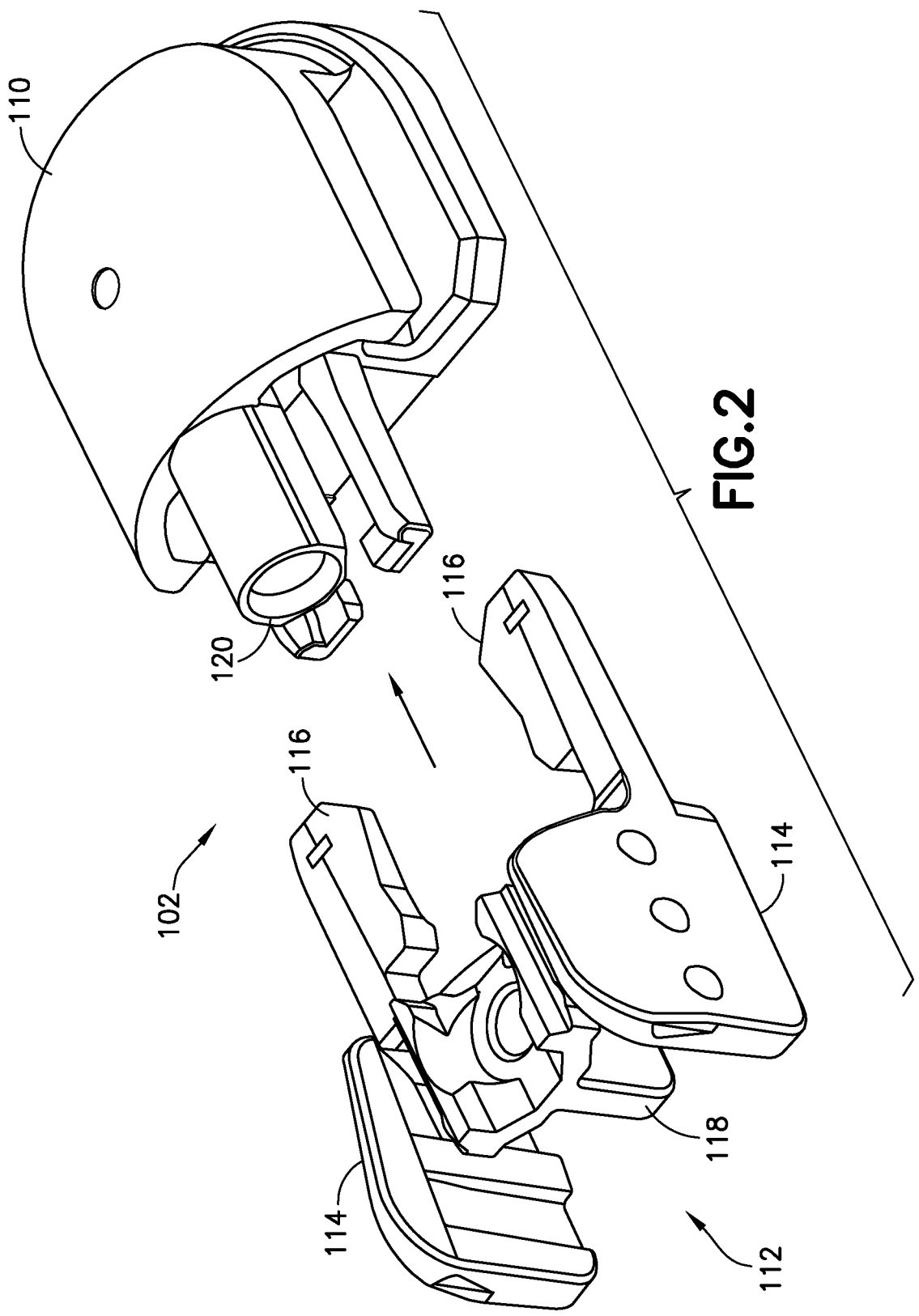
FIG. 2 is an exploded view of a fluid connector of the infusion set of FIG. 1.
Figure 3:
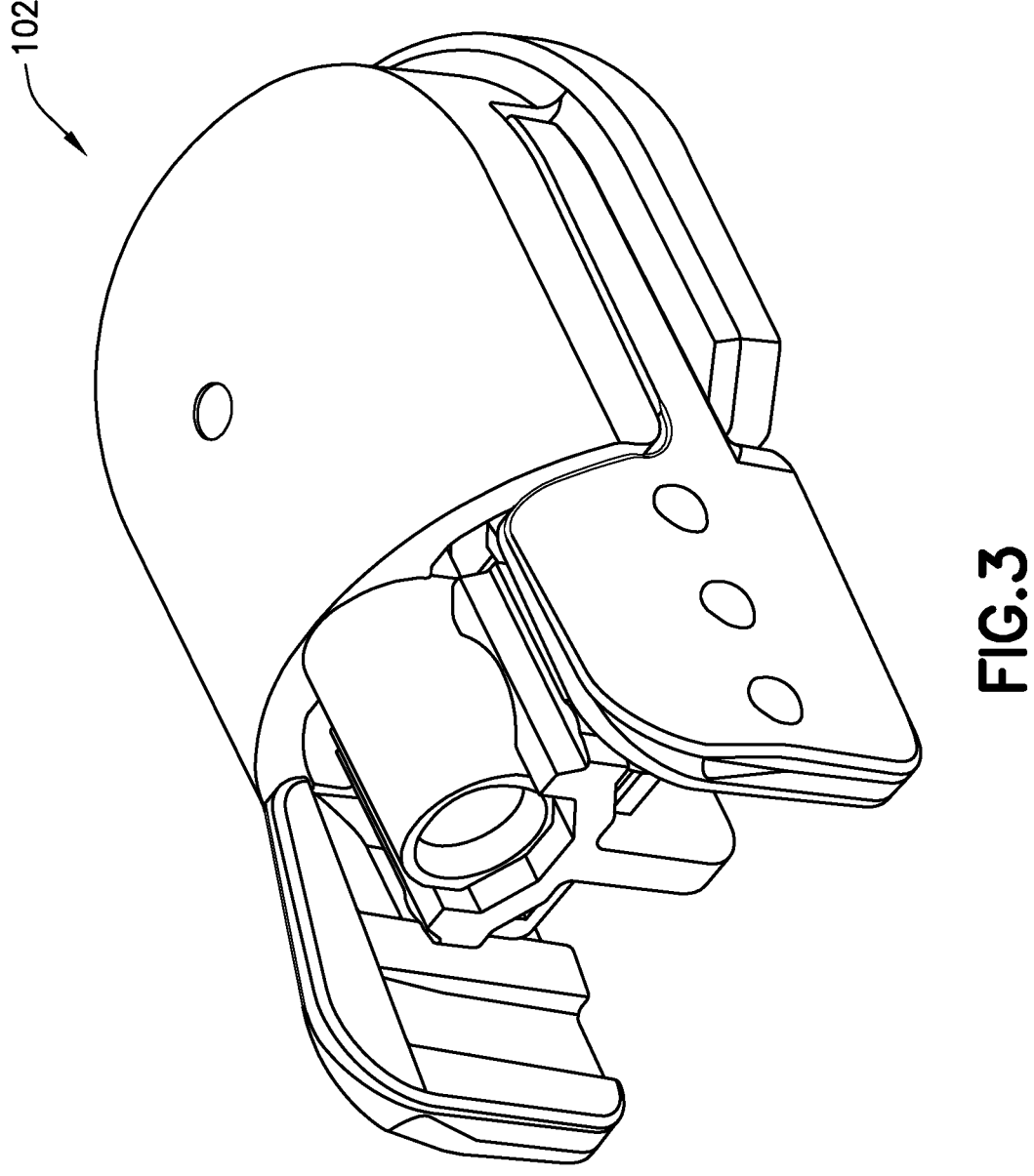
FIG. 3 is a perspective view of the fluid connector of FIG. 2 in an assembled state.

According to one embodiment, the fluid connector 102 is a two-part fluid connector 102. As shown in FIG. 2, the fluid connector 102 includes two components: a fluid path portion 110, and a latching portion 112. The latching portion 112 includes activation levers 114, fluid connector latches 116, and a rigid stop 118.

According to one embodiment, the activation levers 114, fluid connector latches 116, and the rigid stop 118 are integrally formed as a unitary structure. Additionally, the activation levers 114 form arms with their respective fluid connector latches 116. These arms are displaceable relative to the fluid path portion 110. The fluid connector latches 116 are displaceable to a latching position in which the at least a portion of a fluid connector latch 116 of the base 108 is disposed within the fluid path portion 110 (see FIG. 6). Further, the arms are resiliently biased toward the latching position.

The fluid path portion 110 includes a tubing connector portion 120 for connecting the fluid connector 102 with the tubing 104. The fluid path portion 110 can be secured to the latching portion 112 via snap-fit engagement and according to one embodiment, the fluid path portion 110 and the latching portion 112 can be made of the same material. Although the exemplary embodiment of a two-piece fluid connector is illustrated, it will be appreciated by one skilled in the art that a one-piece fluid connector, or a fluid connector made of more than two pieces can be employed without departing from the scope of the present invention.

Figure 4:
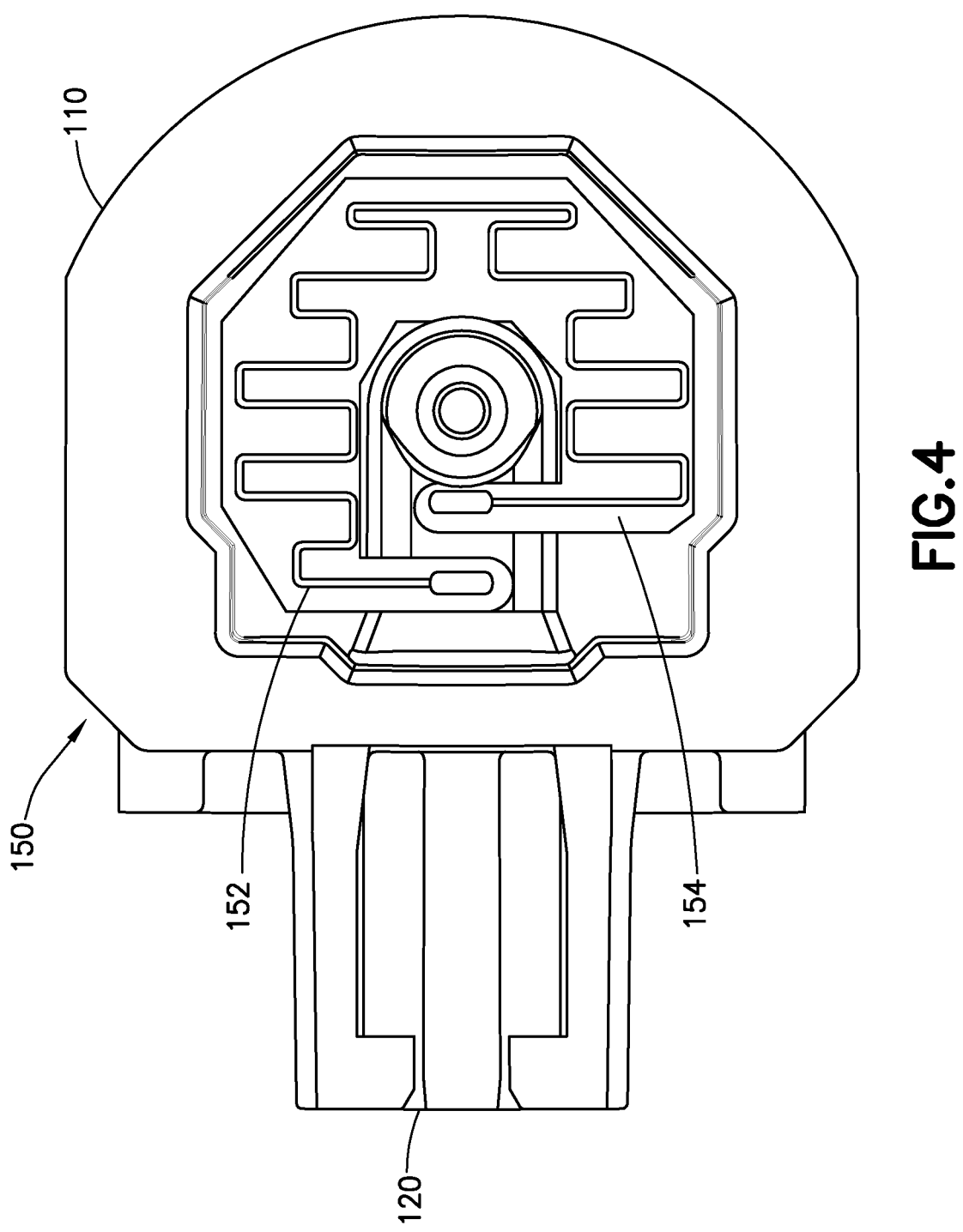
FIG. 4 is a plan bottom view of a fluid path portion of the fluid connector of FIG. 2.
Figure 5:
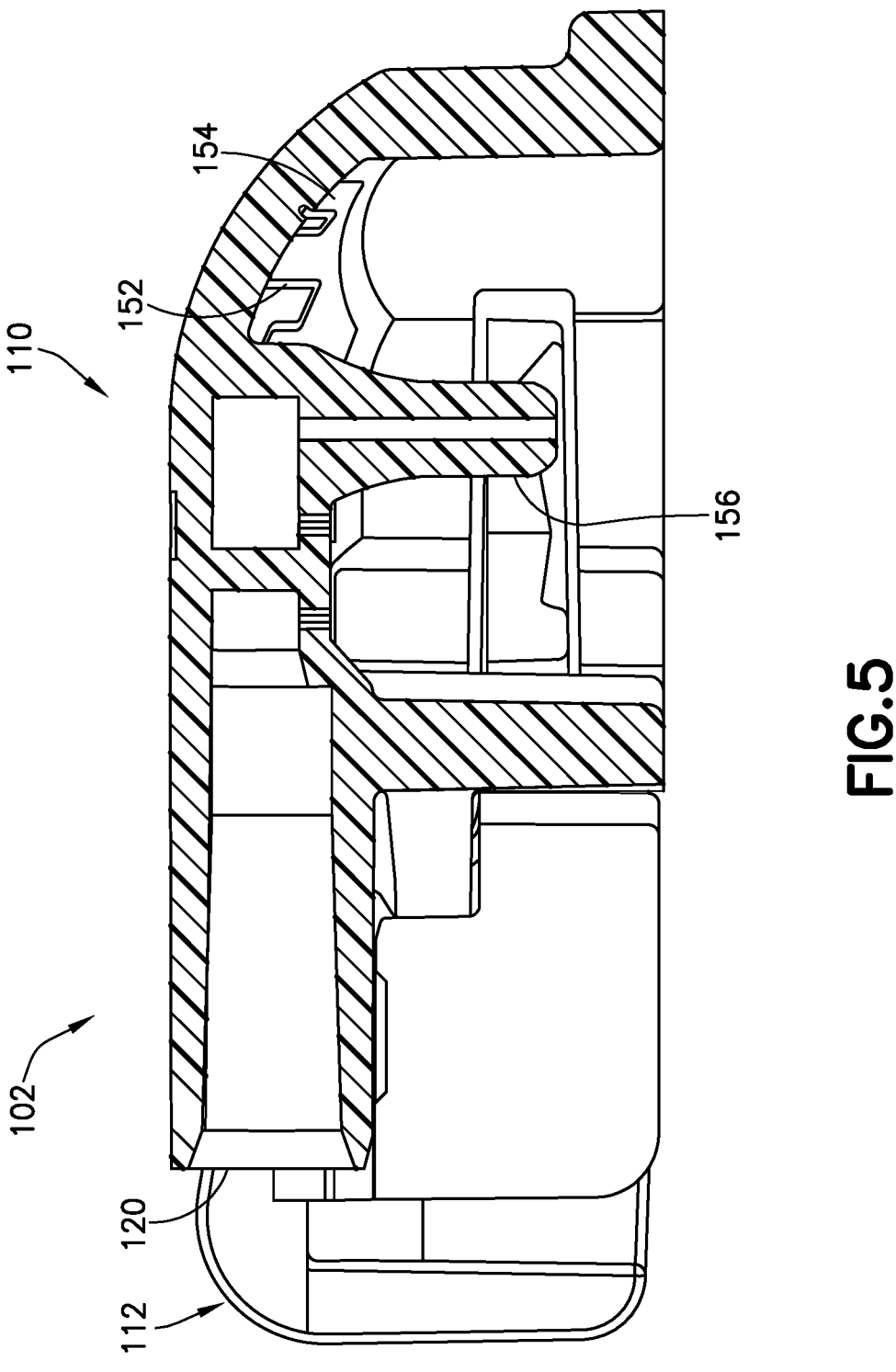
FIG. 5 is a cross-sectional view of the fluid connector of FIG. 2.

FIG. 4 is a plan bottom view of the fluid path portion 110 in accordance with an embodiment of the present invention (with the latching portion omitted for clarity), and FIG. 5 is a cross-sectional view of the fluid connector 102 in accordance with an embodiment of the present invention. As shown in FIGS. 4 and 5, the fluid pathway of the fluid path portion 110 of the fluid connector 102 includes a pathway portion 150, which includes a groove recessed 152 in the top interior ceiling or dome portion or roof an internal dome portion of the fluid path portion 110, and a sealer 154, such as a pressure sensitive adhesive or a membrane or film 154 that covers and fluidly seals the groove 152 to form the pathway portion or fluid connector pathway portion 150. One skilled in the art will understand that other sealers can be employed, such as a molded component that is ultrasonically or chemically welded over the groove 152. For simplicity, in describing this and other embodiments, films are employed as sealers. According to one embodiment, the film 154 is a pressure sensitive adhesive or film 154, such as Mylar, that can fluidly seal the recessed groove 152.

Preferably, the adsorbent, such as activated charcoal adsorbent, is placed in the groove 152 prior to sealing the groove 152 with the film 154. As best shown in FIG. 4, the groove 152 is a torturous path. The groove 152 is configured so that the insulin formulation passing through the adsorbent has a residence time in the pathway portion 150 sufficient to remove the phenolic stabilizing agent from the insulin formulation before delivery to the patient, but also to obtain substantially no denaturing or loss of efficacy of the insulin formulation before delivery to the patient. One skilled in the art will appreciate that other shapes and lengths of the groove 152 can be employed without departing from the scope of the present invention. The goal is to provide sufficient contact with the adsorbent to remove a sufficient amount of the irritation causing stabilizing agent without losing efficacy of the insulin formulation.

As shown in FIG. 6, when the fluid connector 102 is connected with the base 108, a blunt cannula 156, which depends form the ceiling of the domed portion of the fluid connector 102, penetrates a septum 158 of the base 108 to connect the fluid pathway of the fluid connector 102 with the fluid pathway of the base 108.

Figure 7:
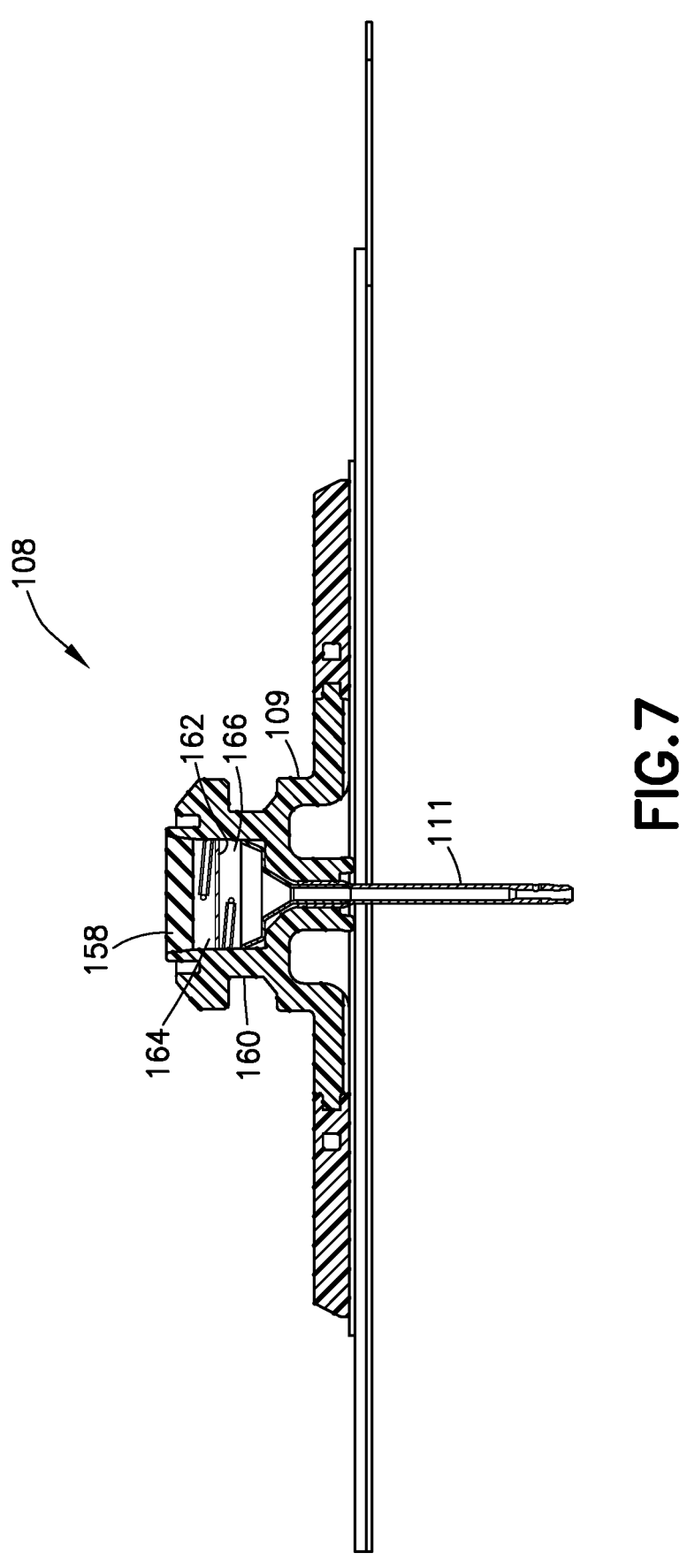
FIG. 7 is a cross-sectional view of a base in accordance with an embodiment of the present invention.
Figure 8:
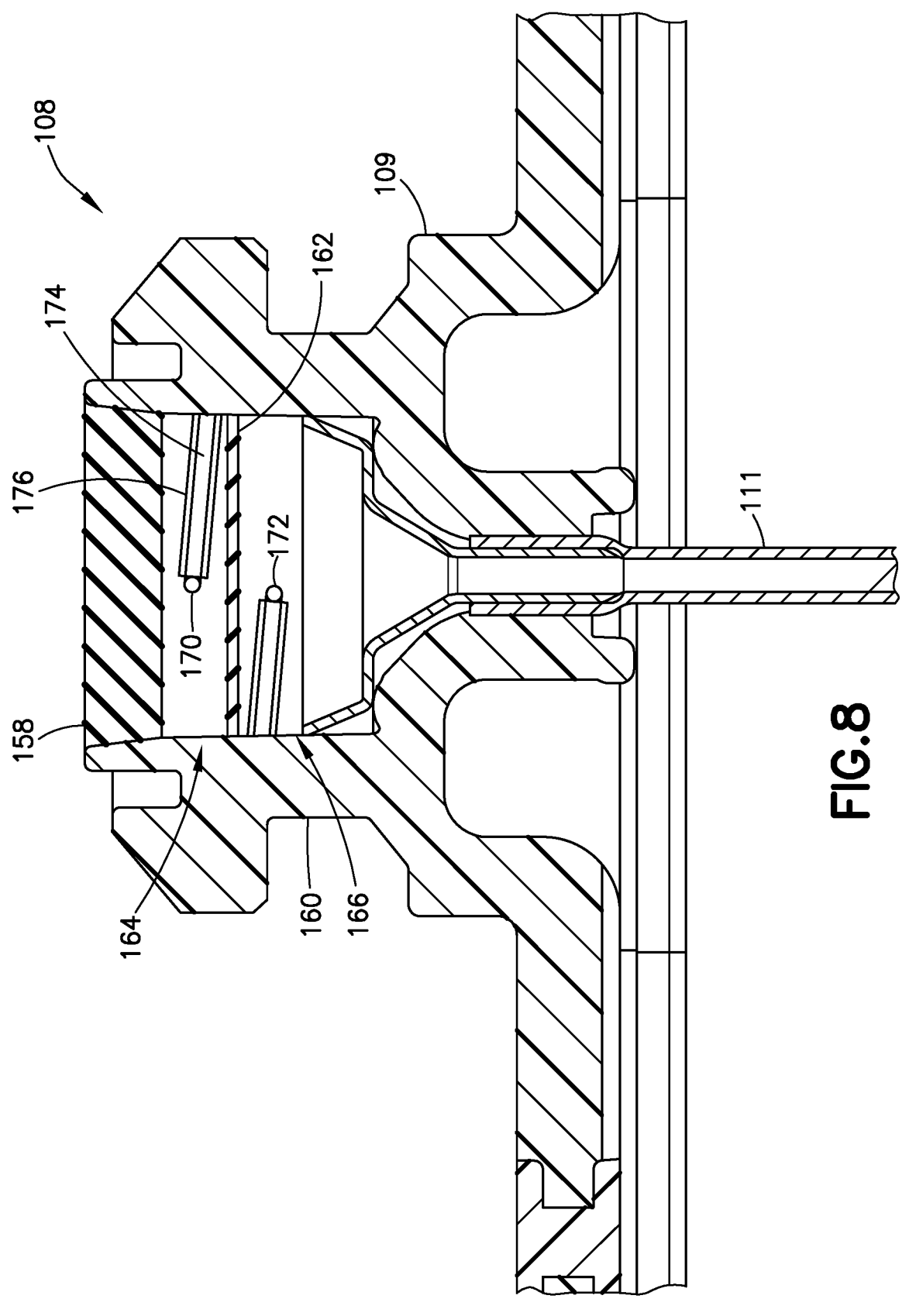
FIG. 8 is an enlarged portion of the base of FIG. 7.

FIG. 7 is a cross-sectional view of the base 108 in accordance with another embodiment of the present invention, and FIG. 8 is an enlarged portion of FIG. 7. As shown in FIGS. 7 and 8, the hollow cannula 111 depends form a distal portion of the base body 109. The base body 109 includes a proximal sealing member 158 fluidly sealing a proximal end of a column portion 160 of the base body 109. According to one embodiment, the proximal sealing member 158 is a septum 158, but other sealing members can be employed without departing from the present invention's scope. The base body 109 also includes a medial sealing member 162 fluidly sealing a medial portion of the column portion 160 and forming a first chamber 164 between the proximal and medial sealing members 158 and 162, and a second chamber 166 between the medial sealing member 162 and a proximal portion of the hollow cannula 111. According to one embodiment, the medial sealing member 162 is a septum 162, but other sealing members can be employed without departing from the present invention's scope.

The first chamber 164 includes a first end port 170 and the second chamber 166 has a second end port 172. The first and second end ports 170 and 172 are connected by a groove 174 recessed in the interior walls of the column portion 160, and the recessed groove 174 is covered by a sealer 176, such as a film 176. Preferably, the adsorbent, such as activated charcoal adsorbent, is placed in the groove 174 prior to sealing the groove 174 with the film 176.

The sealer 176 is preferably a pressure sensitive adhesive or film 176, such as Mylar, that can fluidly seal the recessed groove 174. According to one embodiment, the recessed groove 174 is spiral groove 174. One skilled in the art will appreciate that a plurality of end ports and connecting grooves, or a pair of end ports with a plurality of connecting grooves, or a plurality of end ports, each with a plurality of connecting grooves can be disposed within the column portion without departing from the present invention's scope. But for clarity, only one set of end ports with a single connecting groove is shown in the depicted embodiment.

Figure 9:
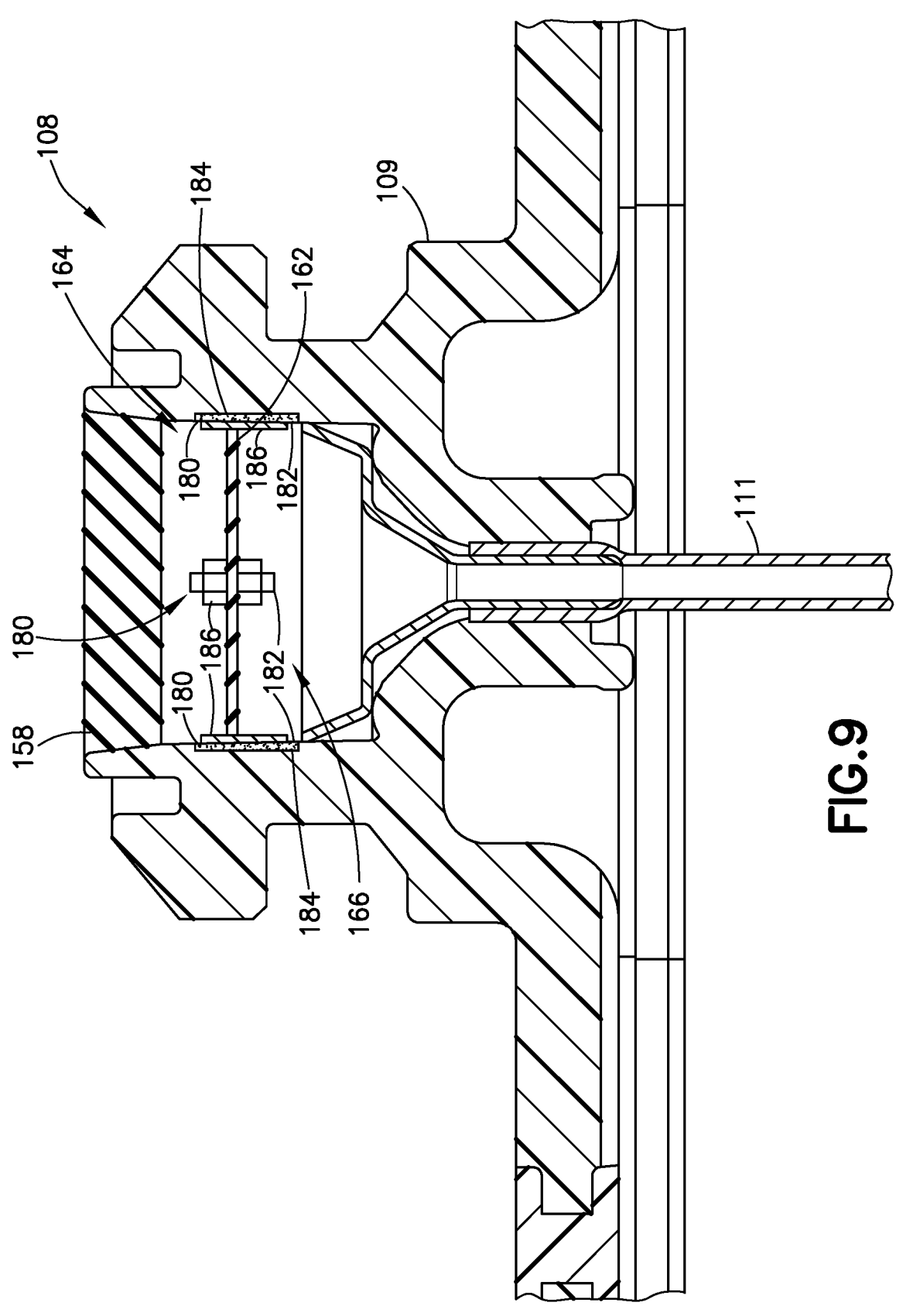
FIG. 9 is an enlarged cross-sectional view of the base 108 in accordance with another embodiment of the present invention.

FIG. 9 is an enlarged cross-sectional view of the base 108 in accordance with another embodiment of the present invention. Like the previous embodiment, as shown in FIG. 9, the base body 109 includes the proximal sealing member 158 fluidly sealing the proximal end of the column portion 160 of the base body 109. The base body 109 also includes the medial sealing member 162 fluidly sealing the medial portion of the column portion 160 and forming the first chamber 164 between the proximal and medial sealing members 158 and 162, and the second chamber 166 between the medial sealing member 162 and a proximal portion of the hollow cannula 111.

The first chamber 164 includes a first end port 180 and the second chamber 166 has a second end port 182. The first and second end ports 180 and 182 are connected by a groove 184 recessed in the interior walls of the column portion 160, and the recessed groove 184 is covered by a sealer 186, such as a film 186. Thus, the groove 184 fluidly connects the first and second chambers 164, 166. Preferably, the adsorbent, such as activated charcoal adsorbent, is placed in the groove 184 prior to sealing the groove 184 with the film 186.

The sealer 186 is preferably a pressure sensitive adhesive or film 186, such as Mylar, that can fluidly seal the recessed groove 184. According to one embodiment, the recessed groove 184 is linear groove 184. Although multiple linear groove 184 are depicted in FIG. 9, one skilled in the art will appreciate that a single linear groove 184 can be employed without departing from the present invention's scope. Additionally, one skilled in the art will appreciate that the grooves 184 do not have to be linear, and can have other shapes without departing form the present invention's scope. For example, the grooves 184 could have a curved and/or a zig-zag shape, or can be a wandering path without a geometric shape.

Figure 10:
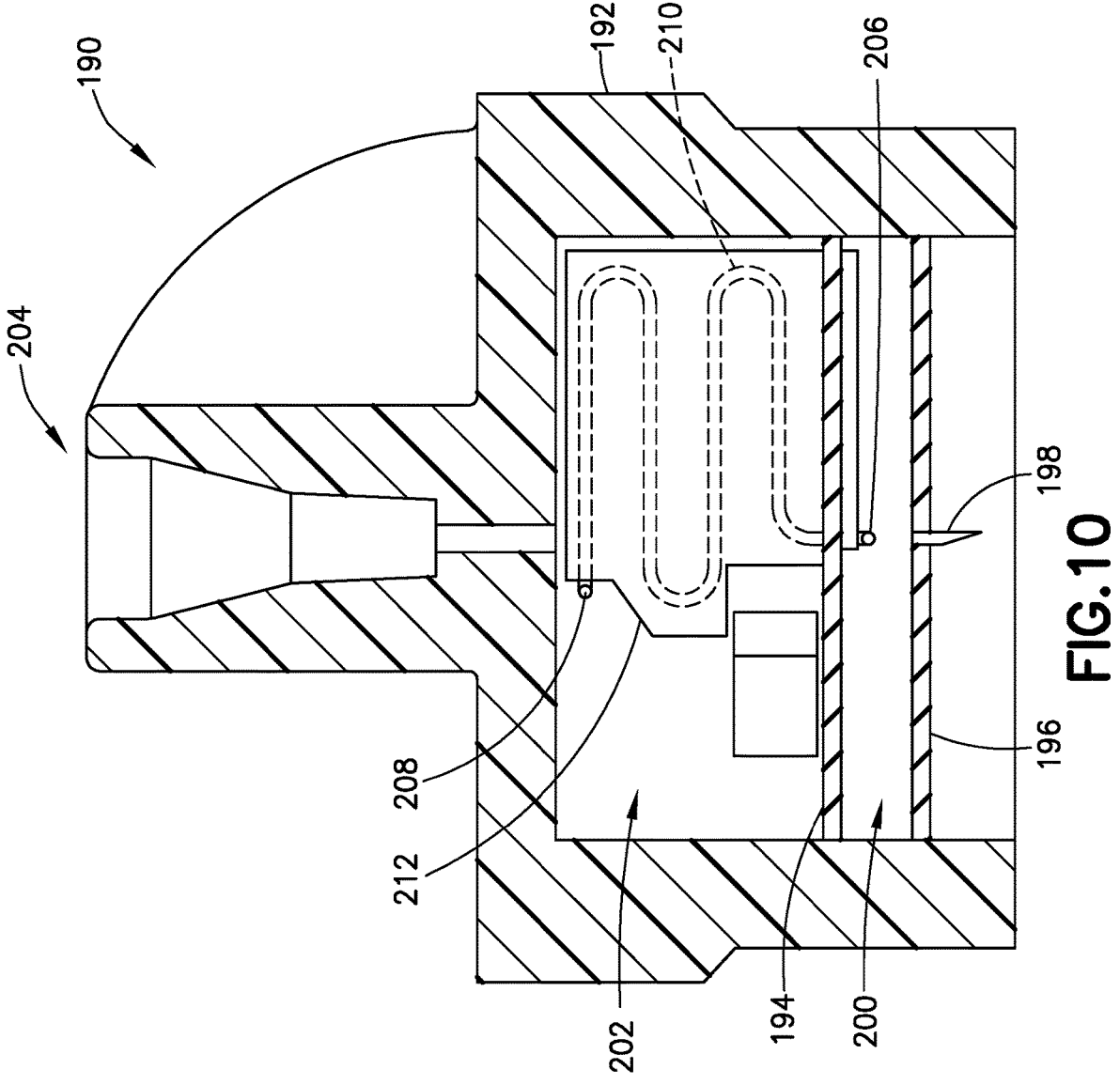
FIG. 10 is a cross-sectional view of a pump connector in accordance with an embodiment of the present invention.

FIG. 10 is a cross-sectional view of a pump connector 190 in accordance with an embodiment of the present invention. The connector 190 includes a main body 192 with a medial sealing member 194, a proximal sealing member 196, and a connector needle 198 proximally depending from the proximal sealing member 196 for fluidly communicating with a pump. The connector needle 198 fluidly connects with a first chamber 200 disposed between the medial and proximal sealing members 194 and 196. The connector 190 also has a second chamber 202 disposed distally (toward the patient) of the medial sealing member 194. The second chamber 202 fluidly connects with a tubing port 204 for connecting with tubing of a medicament delivery device.

The connector 190 also includes a first end port 206 disposed in the first chamber 200, a second end port 208 disposed in the second chamber 202, and a recessed groove 210 connecting the first and second end ports 206 and 208.

The recessed groove 210 fluidly connects the first and second chambers 200, 202. The recessed groove 210 is recessed from an internal wall of the connector 190, and is covered by sealer 212, such as a film 212. Preferably, the adsorbent, such as activated charcoal adsorbent, is placed in the groove 210 prior to sealing the groove 210 with the film 212. The film 212 is preferably a pressure sensitive adhesive or film 212, such as Mylar, that can fluidly seal the recessed groove 210.

According to one embodiment, the recessed groove 210 is linear. According to another embodiment, the recessed groove 210 is a spiral. According to another embodiment depicted in FIG. 10, the recessed groove 210 is wandering path without a particular geometric shape. Such a path can be advantageous to increase dwelling time of a medicament within the recessed groove 210.

Although only one pair of end ports 206, 208 and one recessed groove 210 is depicted in FIG. 10, one skilled in the art will appreciate that a plurality of end ports and connecting grooves, or a pair of end ports with a plurality of connecting grooves, or a plurality of end ports, each with a plurality of connecting grooves can be disposed within the inventive connector without departing from the present invention's scope.

Figure 11:
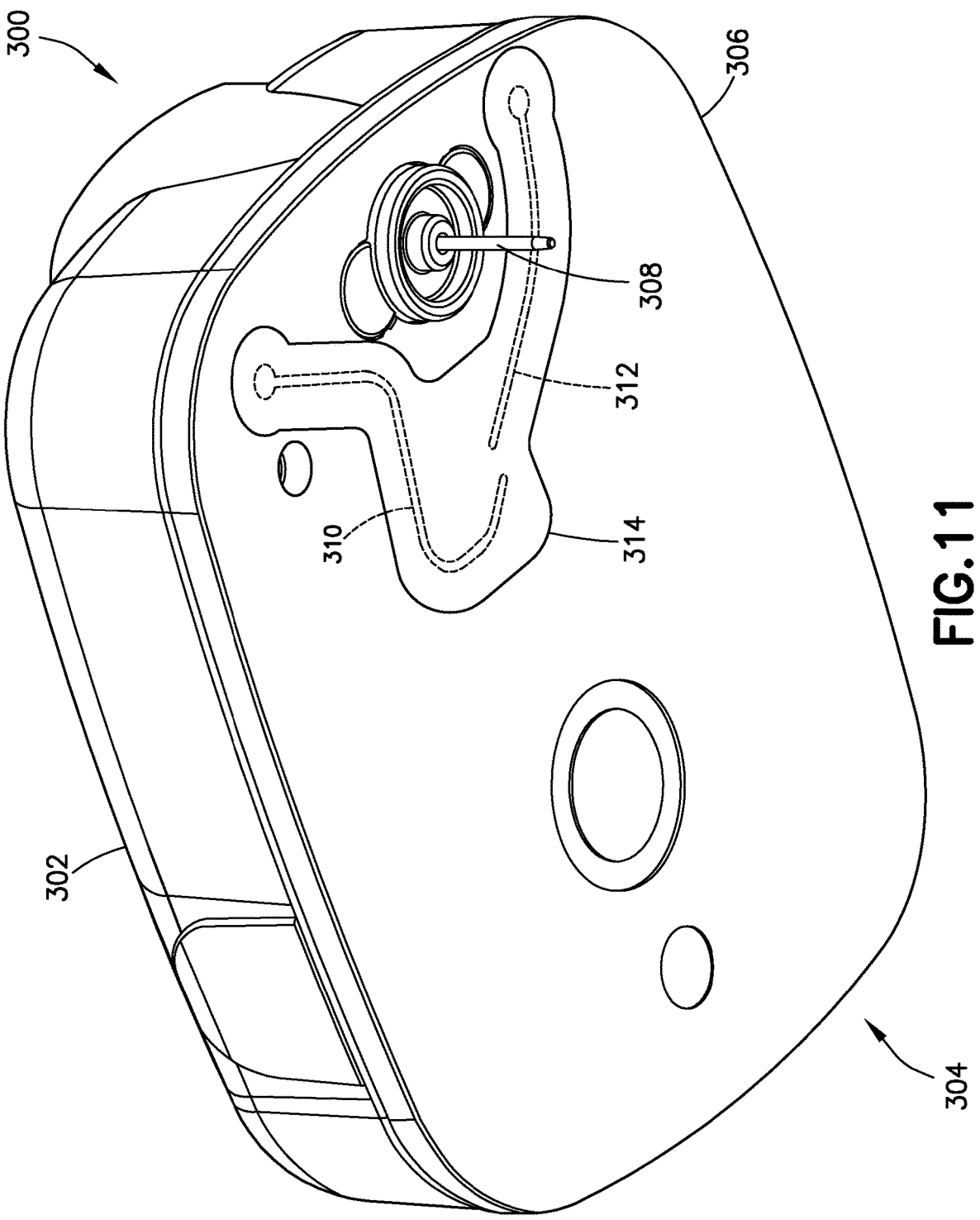
FIG. 11 is a perspective view of a patch injector in accordance with another embodiment of the present invention.

FIG. 11 is a bottom perspective view of a patch injector 300 in accordance with another embodiment of the present invention. The patch injector 300 includes a cover 302 and a base 304 having a base body 306 and a hollow cannula 308 for insertion into a patient. According to one embodiment, the hollow cannula 308 is rigid and sharpened. According to another embodiment, the hollow cannula 308 is flexible and the patch injector 300 also includes a sharpened insertion needle for inserting the hollow cannula 308 into a patient. According to one embodiment, the hollow cannula 308 is fixed relative to the base body 306. Preferably, however, the hollow cannula 308 is movable relative to the base body 306 from a retracted position, in which the hollow cannula 308 does not extend distally beyond the base body 306, to a patient insertion position, in which in which the hollow cannula 308 does extend distally beyond the base body 306, as shown in FIGS. 11 and 12.

According to one embodiment, the patch injector 300 includes a reservoir holding the fluid, such as insulin. The patch injector 300 includes a fluid pathway fluidly connecting the reservoir with the hollow cannula 308. According to one embodiment, the base body 306 includes one or more grooves 310, 312 recessed from a surface of the base body 306, and a sealer 314, such as film 314, seals the grooves 310, 312 forming a pathway portion of the fluid pathway. The manufacturer preferably provides an adsorbent, such as activated charcoal adsorbent, in the grooves 310, 312 prior to sealing the grooves 310, 312 with the sealer 314. such as a film 314.

The sealer 314 is preferably a pressure sensitive adhesive film 314, such as Mylar, that can fluidly seal the recessed groove or grooves 310, 312.

Figure 12:
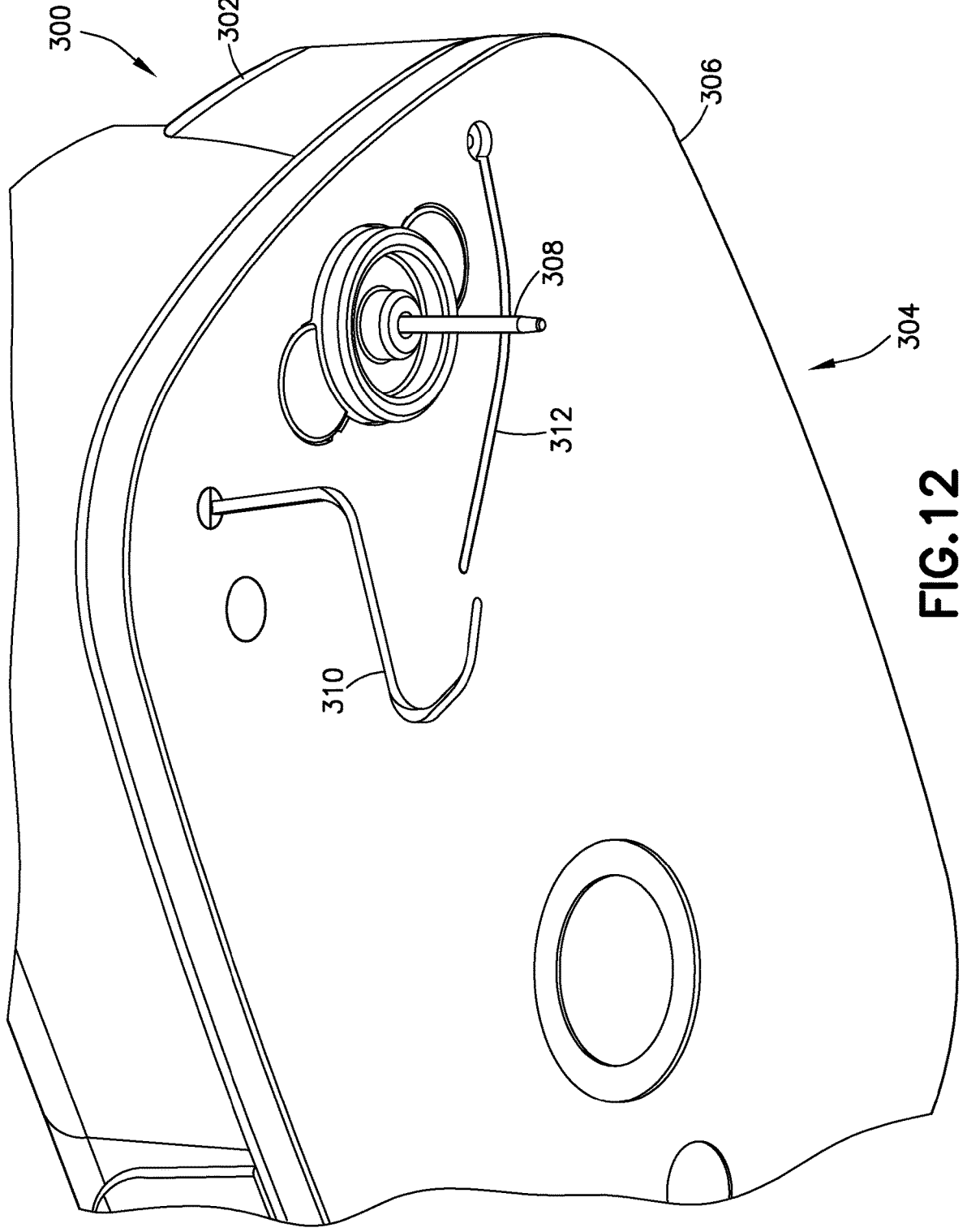
FIG. 12 is a partial perspective view of the patch injector of FIG. 11 with a sealer removed for illustration.

FIG. 12 omits the film 314 to better illustrate the grooves 310, 312. According to one embodiment depicted in FIGS. 11 and 12, the grooves are proximally recessed from a distal surface of the base body 306. In such an embodiment, because the pathway portion is disposed outside the cover 302, the fluid pathway passes from an interior to an exterior, and in the embodiment of FIGS. 11 and 12, the fluid pathway passes back into an interior of the patch injector 300 prior to reaching the hollow cannula 308. According to another embodiment, the grooves are disposed inside the cover 302, distally recessed from a proximal surface of the base body

9

10

306. A size and shape of the groove or grooves 310, 312 is operable to provide a residence time in the groove for the fluid, such as an insulin formulation, passing through the activated charcoal absorbent to minimize or prevent denaturing and/or loss of efficacy before delivery to the patient.

As in other depicted and described embodiments, during operation of the patch injector 300, the adsorbent removes one or more compounds or substances from the fluid prior to delivery of the fluid to the patient through the hollow cannula 308.

Figure 13:
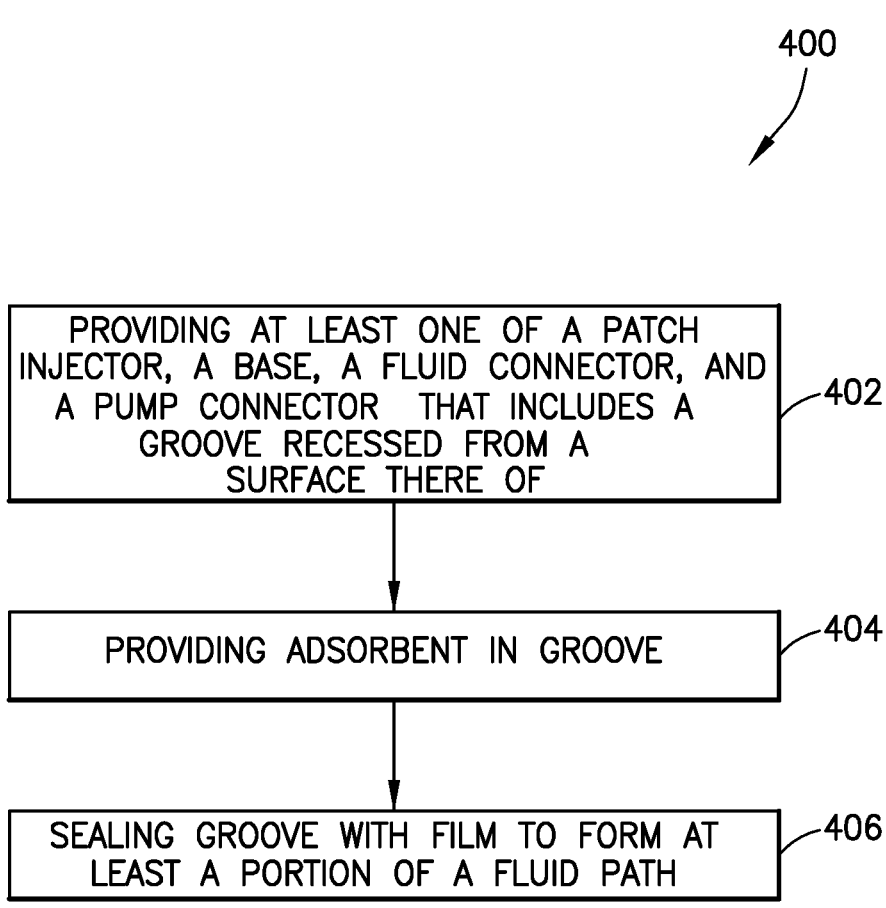
FIG. 13 is a flowchart of a method in accordance with an embodiment of the present invention.

FIG. 13 is a flowchart of a method 400 in accordance with an embodiment of the present invention. In the first operation. For illustrative purposes, the method is described as being implemented by a manufacturer, but it will be understood that other entities can practice the method without departing from the present invention's scope. In operation 402, the manufacturer provides at least one of a base, a fluid connector, and a pump connector of an infusion set, and the at least one of the base, the fluid connector, and the pump connector includes a groove recessed from an internal surface thereof. In operation 404, the manufacturer provides an adsorbent in the groove. And in operation 406, the manufacturer seals the groove with a film to form at least a portion of a fluid path.

The method can include additional operations. For example, in a base or a pump connector, the method can include inserting a medial sealing member between first and second end ports of the groove. The method can also include inserting another sealing member sealing or at least limiting access to the first end port from an external environment.

Embodiments of the present invention have been described with respect to multi-part infusion sets and patch injectors, but embodiments of the present invention could also include other medicament delivery devices, such as one-piece infusion sets. For brevity, however, these embodiments have been omitted.

Although only a few embodiments of the present invention have been shown and described, the present invention is not limited to the described embodiments. Instead, it will be appreciated by those skilled in the art that changes may be made to these embodiments without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

Various aspects of the embodiments may be employed independently or in combinations thereof.

The invention claimed is:

1. A medical device operable to deliver a fluid to a patient, comprising at least one of:

a base having a base body and a hollow cannula for insertion into a patient, the hollow cannula being one of fixed to the base body and movable relative to the base body to a patient insertion position; and a pump connector connectable to a pump;

wherein:

the at least one of the base body and the pump connector includes a fluid pathway therethrough;

the fluid pathway of the at least one of the base body and the pump connector includes a sealing member fluidly sealing a first chamber from a second chamber;

the first chamber includes a first end port and the second chamber includes a second end port, the first and second end ports being fluidly connected by a pathway portion housing an adsorbent operable to modify a fluid traversing the pathway portion by removing one or more compounds or substances from the fluid prior to delivery of the fluid to the patient, the pathway portion being sealed with a sealer.

2. The device according to claim 1, wherein the pathway portion is formed by a recessed groove.

3. The device according to claim 2, wherein the adsorbent comprises an activated charcoal adsorbent.

4. The device according to claim 3, wherein the fluid comprises an insulin formulation containing a phenolic stabilizing agent, and where the activated charcoal adsorbent is adapted to remove the phenolic stabilizing agent from the insulin formulation before delivery to the patient.

5. The device according to claim 4, wherein a size and shape of the groove is operable to provide a residence time in the groove for the insulin formulation passing through the activated charcoal absorbent to minimize or prevent at least one of denaturing and loss of efficacy before delivery to the patient.

6. The device according to claim 4, wherein the activated charcoal adsorbent comprises a phosphoric acid treated activated charcoal adsorbent.

7. The delivery according to claim 4, wherein the phenolic stabilizing agent is selected from the group consisting of phenol, m-cresol, and mixtures thereof.

8. The device according to claim 1, wherein the sealer comprises a film that forms a portion of the pathway portion.

9. A medical device operable to deliver a fluid to a patient, comprising:

a base having a hollow cannula for insertion into a patient, and a base body attached to the hollow cannula;

a fluid connector connectable to the base;

a pump connector connectable to a pump; and tubing connecting the fluid connector and the pump connector;

wherein:

each of the base body, the fluid connector, the pump connector, and the tubing has a fluid pathway therethrough, the respective fluid pathways being fluidly connectable;

the fluid pathway of at least one of the base body, the fluid connector, and the pump connector includes a pathway portion sealed with a sealer;

the pathway portion includes an adsorbent operable to modify a fluid traversing the pathway portion by removing one or more compounds or substances from the fluid prior to delivery of the fluid to the patient;

the pathway portion comprises a groove recessed from an internal surface of the fluid connector;

the groove is recessed from a roof of an internal dome portion of the fluid connector;

the fluid connector includes a hollow cannula depending from the roof of the internal dome portion; and the groove fluidly connects an incoming fluid path with a cannula fluid path of the fluid connector.

10. The device according to claim 9, wherein the adsorbent comprises an activated charcoal adsorbent.

11. The device according to claim 10, wherein the fluid comprises an insulin formulation containing a phenolic stabilizing agent, and where the activated charcoal adsorbent is adapted to remove the phenolic stabilizing agent from the insulin formulation before delivery to the patient.

12. The device according to claim 11, wherein a size and shape of the groove is operable to provide a residence time in the groove for the insulin formulation passing through the activated charcoal absorbent to minimize or prevent at least one of denaturing and loss of efficacy before delivery to the patient.

13. The device according to claim 11, wherein the activated charcoal adsorbent comprises a phosphoric acid treated activated charcoal adsorbent.

14. The delivery according to claim 11, wherein the phenolic stabilizing agent is selected from the group consisting of phenol, m-cresol, and mixtures thereof.

15. The device according to claim 9, wherein the sealer comprises a film that forms a portion of the pathway portion.

16. A medical device operable to deliver a fluid to a patient, comprising:
   a base having a hollow cannula for insertion into a patient, and a base body attached to the hollow cannula;
   a fluid connector connectable to the base;
   a pump connector connectable to a pump; and
   tubing connecting the fluid connector and the pump connector;
   wherein:
      each of the base body, the fluid connector, the pump connector, and the tubing has a fluid pathway therethrough, the respective fluid pathways being fluidly connectable;
      the fluid pathway of at least one of the base body, the fluid connector, and the pump connector includes a pathway portion sealed with a sealer;
      the pathway portion includes an adsorbent operable to modify a fluid traversing the pathway portion by removing one or more compounds or substances from the fluid prior to delivery of the fluid to the patient;
      the pathway portion comprises a groove recessed from an internal surface of the base body;
      the hollow cannula depends from a distal portion of the base body;
      the base body includes a proximal sealing member fluidly sealing a proximal end of a column portion of the base body, and a medial sealing member fluidly sealing a medial portion of the column portion and forming a first chamber between the proximal and medial sealing members, and a second chamber between the medial sealing member and a proximal portion of the hollow cannula;
      the groove is recessed from an internal surface of the column portion; and
      the groove fluidly connects the first and second chambers.

17. A medical device operable to deliver a fluid to a patient, comprising:
   a base having a hollow cannula for insertion into a patient, and a base body attached to the hollow cannula;

a fluid connector connectable to the base;
   a pump connector connectable to a pump; and
   tubing connecting the fluid connector and the pump connector;
   wherein:
      each of the base body, the fluid connector, the pump connector, and the tubing has a fluid pathway therethrough, the respective fluid pathways being fluidly connectable;
      the fluid pathway of at least one of the base body, the fluid connector, and the pump connector includes a pathway portion sealed with a sealer;
      the pathway portion includes an adsorbent operable to modify a fluid traversing the pathway portion by removing one or more compounds or substances from the fluid prior to delivery of the fluid to the patient;
      the pathway portion comprises a groove recessed from an internal surface of the pump connector
      the pump connector includes a medial sealing member fluidly separating an incoming chamber and an outgoing chamber within the pump connector;
      the groove is recessed form an internal wall of the pump connector; and
      the groove fluidly connects the incoming and outgoing chambers of the pump connector.

18. A method of manufacturing a medical device, comprising:
   providing at least one of a patch injector, a base, a fluid connector, and a pump connector that includes a groove recessed from a surface of the at least one of the patch injector, the base, the fluid connector, and the pump connector;
   providing an adsorbent in the groove; and
   sealing the groove with a sealer to form at least a portion of a fluid path through the at least one of the patch injector, the base, the fluid connector, and the pump connector.

19. The method according to claim 18, wherein the sealer comprises a film that forms a portion of the pathway portion.

20. A medical device operable to deliver a fluid to a patient, comprising at least one of:
   a base having a base body and a hollow cannula for insertion into a patient, the hollow cannula being one of fixed to the base body and movable relative to the base body to a patient insertion position; and
   a pump connector connectable to a pump;
   wherein the at least one of the base body and the pump connector includes a fluid pathway therethrough;
   the fluid pathway of the at least one of the base body and the pump connector includes a sealing member partitioning a first chamber from a second chamber, the first chamber and the second chamber being fluidly bridged by a film-sealed groove housing an adsorbent operable to modify a fluid traversing the groove by removing one or more compounds or substances from the fluid prior to delivery of the fluid to the patient.

* * * * *